United States Patent [19]
Brigati et al.

[11] Patent Number: 5,116,732
[45] Date of Patent: May 26, 1992

[54] TETRAZOLIUM HALIDE COMPOUNDS AND METHODS

[75] Inventors: David J. Brigati, Edmond, Okla.; Sreeramulu Nagubandi, New City, N.Y.; Massoud Arvanaghi, Hackensack, N.J.

[73] Assignee: Fisher Scientific Co., Pittsburgh, Pa.

[21] Appl. No.: 405,754

[22] Filed: Sep. 11, 1989

[51] Int. Cl.$^5$ .................. C12Q 1/32; C12Q 1/00; C02D 257/04; C02D 257/10

[52] U.S. Cl. .................. 435/26; 435/4; 435/25; 435/29; 435/960; 548/250; 548/252; 548/254

[58] Field of Search .............. 430/154; 435/5, 7, 25, 435/960, 4, 26, 29; 548/254, 250, 252

[56] References Cited

U.S. PATENT DOCUMENTS

| | | | |
|---|---|---|---|
| 3,881,930 | 5/1975 | Schleigh | 96/48 R |
| 3,887,372 | 6/1975 | Bailey | 96/48 R |
| 3,887,374 | 6/1975 | Brongo et al. | 96/48 R |
| 3,957,514 | 5/1976 | Adin | 96/48 R |
| 4,284,704 | 8/1981 | Fleming et al. | 430/154 |
| 4,731,335 | 3/1988 | Brigati | 436/180 |
| 4,792,521 | 12/1988 | Shochat | 435/7 |

OTHER PUBLICATIONS

Chemical Abstract CA 110(23):208931b 1987.
E. Seidler, "New nitro-monotetrazolium salts and their use in histochemistry" Histo chem. Journal, vol. 12, pp. 619-630 (1980).
F. P. Altman, "Tetrazolium Salts and For Formazans", Prog. Histochem. Cytochem. vol. 9, pp. 1-56 (1976).
F. P. Altman, "Tetrazolium salts: a consumer's guide," Histochem. Journal, vol. 8, pp. 471-485 (1976).
E. P. Unger et al., "Automation of in situ hybridization" J. of Histotechnology, vol. 11, No. 4, pp. 253-258 (1988).

*Primary Examiner*—Christine Nucker
*Assistant Examiner*—David R. Preston
*Attorney, Agent, or Firm*—Alan M. Doernberg

[57] ABSTRACT

Compounds of the formula DNB-TZ(P2) (P3) X, wherein TZ is a tetrazolium ring, DNB is 5-(2,4-dinitrophenyl), X is halide and P2 and P3 are each independently halophenyl, nitrophenyl or phenyl. The compound INDT 2-(4-iodophenyl)-3-(4-nitrophenyl)-5-(2,4-dinitrophenyl) tetrazolium bromide exhibits facile reduction to insoluble chromophoric formazan compared to the chromagen INT. INDT differs structurally from INT 2-(4-iodophenyl)-3-(4-nitrophenyl)-5-phenyltetrazolium chloride by having 2,4-dinitrophenyl instead of phenyl at the 5-position on the tetrazolium ring. The compounds, including INDT, are useful as chromagens for histological staining, as well as in enzyme-amplified staining as a part of immunological or hybridization assays.

16 Claims, No Drawings

TETRAZOLIUM HALIDE COMPOUNDS AND METHODS

BACKGROUND OF THE INVENTION

The present invention relates to tetrazolium chromagens and their use in histological staining and in enzyme amplified assays.

Tetrazolium halides have been widely used as stains, especially in histology. Such compounds have a cationic tetrazolium ring, three phenyl substituents at the 2, 3 and 5 positions on the ring and a halide anion (often chloride or bromide). The chromagen is reduced to a formazan, which is strongly colored and is insoluble in water. For the derivatives with one, two or three 4-nitrophenyl substituents (and correspondingly two, one or no phenyl substituents), the ease of reduction to formazan increases with increasing numbers of nitrophenyl substituents. Literature references indicate that a 4-nitrophenyl substituent attached to the 2-position or 3-position of the tetrazolium ring increases the reducibility to a greater extent than does the same group linked to the 5-position of the tetrazolium ring. One reference suggests that, in fact, a 4-nitrophenyl group attached at the 5-position of the tetrazolium ring has the opposite effect compared to that same group attached to the 2-position or 3-position. See F.P. Altman, Prog. Histochem. Cytochem., vol. 9, pp. 1–56 (1976); F.P. Altman, Histochem. J., vol. 8, pp. 471–85 (1976); E. Seidler, Z. Med. Labortechnik, vol. 9, pp. 241–51 (1968); Histo-Und Zytochemie Dehydrierender Enzyme; Grundlagen Und Problematik (F. Wohlrab et al, eds., (1979), pp. 9–159 and 257–92; and E. Seidler, Histochem. J., vol. 12, pp. 619–30 (1980).

A widely used tetrazolium halide is 2-[4-iodophenyl]-3-[4-nitrophenyl]-5-phenyltetrazolium chloride, known as INT. INT has the advantages of high stability in aqueous solutions. Once reduced to the corresponding formazan, a strong reddish-brown color is formed. The formazan is stable to reoxidation or dissolution and is therefore a very satisfactory histological stain.

INT has also been used as chromagen to develop an enzyme localized on tissue (whether localized by antigenic determinants or by hybridization on nucleic acids). For example, the localized enzyme alkaline phosphatase (AP) hydrolizes 5-bromo-4-chloro-3-indolylphosphate (known as BCIP) to a reactive intermediate, which reduces INT to the formazan. Thus, when tissue with localized AP is contacted with BCIP and INT in aqueous media (the chromagen), reaction occurs leading to the red formazan being deposited on the tissue in the vicinity of the localized enzyme. See J. McGadey, J. Med. Lab. Technol. vol. 24, pp. 126–28 (1967); J. McGadey, Histochemie, vol. 23, pp. 180–84 (1970).

While INT is a satisfactory chromagen for both histological staining and such enzymatic assays, its reduction to formazan is somewhat difficult. In some situations, that results in some spreading of the reaction product away from the desired site (i.e., the site of immobilized AP enzyme).

BRIEF DESCRIPTION OF THE INVENTION

Tetrazolium halides have been discovered having 2,4-dinitrophenyl at the 5-position on the tetrazolium ring. This substituent (especially compared to phenyl at that position) leads to more facile reduction to the formazan.

Accordingly, the present invention provides a compound of the formula DNB-TZ(P2)(P2) X, wherein TZ is a tetrazolium ring, DNB is 5-(2,4-dinitrophenyl), X is halide and P2 and P3 are each independently halophenyl, dinitrophenyl, nitrophenyl or phenyl. Such compounds can be shown more fully by the formula:

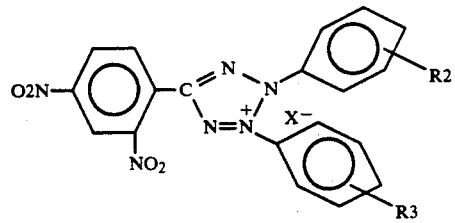

The phenyl in the 5-position (on the carbon) is substituted by 2,4-dinitrophenyl. The phenyls in the 2 and 3 positions may be unsubstituted [R2 or R3 being H) or substituted by halogen or nitro (once or multiple places), generally once in the 4 (para) position. The halide X is generally Br or Cl, but can be I.

The present invention also provides a method for staining tissue which comprises:

a) contacting tissue with the above tetrazolium compound, and b) reducing the tetrazolium compound to formazan to stain the tissue.

DETAILED DESCRIPTION OF THE INVENTION

The present invention can be illustrated by reference to the preferred compound INDT: 2-(4-iodophenyl)-3-(4-nitrophenyl)-5-[2,4-dinitrophenyl) tetrazolium bromide. Such is the compound of the above formula wherein R2 is I, R3 is nitro and X is Br. The general principles of synthesis and use will apply to other compounds of that formula.

The first step of synthesis is to react 2,4-dinitrobenzaldehyde with a phenylhydrazine (with p-nitrophenylhydrazine to make INDT). That reaction, in a solvent mixture such as ethanol/hydrochloric acid, results in a hydrazone intermediate:

DNT—CH=N—NH—Ph—R3 where DNT is 2,4-dinitrophenyl, Ph is phenylene (preferably 1,4-phenylene) and R3 is the substituent desired on the 3-phenyl (nitro in the case of INDT). The amine R2—Ph—NH2 can then be converted (with sodium nitrite and HCl) to the corresponding phenyl diazonium chloride which can be reacted with the hydrozone intermediate (in dimethylformamide/pyridine) to yield the formazan. The formazan can then be oxidized by adding N-bromosuccinamide to form the tetrazolium salt.

Such synthesis corresponds generally to that described in E. Seidler, Histochem. J., vol. 12, pp. 619–30 (1980) to produce INT, except that dinitrophenyl benzaldehyde is used in place of benzaldehyde to form the hydrazone intermediate and other minor modifications.

If R3 is to be H, Cl, I or Br (rather than nitro), then the corresponding phenylhydrazine can be used in forming the hydrazone intermediate. If R2 is to be H, Cl, Br or nitro (rather than I), then the corresponding phenylamine can be reacted with sodium nitrite. It should be appreciated that the 2-position and 3-position are equivalent on the tetrazolium ring (due to resonance). Therefore, if R2 and R3 are to be different, one can choose which should be introduced as phenylhydrazine and which should be introduced as phenylamine based upon ease of synthesis and availability of starting materials.

Exemplary 5-(2,4-dinitrophenyl)-tetrazolium halides can be illustrated with the following chart:

| Compound | 2-position | 3-position | X |
|---|---|---|---|
| INDT | iodophenyl | 4-nitrophenyl | bromide |
| INDT | iodophenyl | 4-nitrophenyl | chloride |
| IDDT | iodophenyl | 2,4-dinitrophenyl | bromide |
| IDDT | iodophenyl | 2,4-dinitrophenyl | chloride |
| I(2-N)DT | iodophenyl | 2-nitrophenyl | bromide |
| I(2-N)DT | iodophenyl | 2-nitrophenyl | chloride |
| IPDT | Iodophenyl | phenyl | bromide |
| IPDT | Iodophenyl | phenyl | chloride |

In addition, at 2-position, instead of iodophenyl the compound can have a bromophenyl group.

EXAMPLES

Example 1

Preparation of INDT

The following reactants were dissolved by warming in 50 ml of a 2:2:1 mixture (by volume) of ethanol, water and concentrated hydrochloric acid:

1.96 g of 2,4-dinitrobenzaldehyde (from Aldrich)

1.53 g of p-nitrophenylhydrazine (from Aldrich). After mixing with stirring for one hour, the hydrazone derivative formed was recovered as a solid by precipitation. The product was washed with excess distilled water and vacuum dried at room temperature yield was 2.5 g.

4-iodophenylamine (1.1 g) was then reacted with 0.5 g sodium nitrite and HCl in an ice bath (0-5 deg C.) to form a diazonium chloride. To 1.65 g of the hydrazone derivative in 200 ml of a 1:1 mixture (by volume) of dimethylformamide and pyridine was then added all of the diazonium chloride at 0-5 deg C. with stirring. The reaction proceeded for 0.5 hour under 0-5 deg C. conditions. After alkaline treatment and acidification the resultant brick red formazan derivative was recovered by filtration. After vacuum drying at room temperature, the yield was 2.4 g.

Next 300 mg of N-bromosuccinamide was added to 1.5 g of the formazan derivative in 200 ml ethyl acetate. After reaction for 0.5 hour under reflux conditions, the product tetrazolium salt was recovered by precipitation with ether as a yellow powder. It was purified by recrystallization from acetone-methanol after charcoal treatment of the hot solution, by pouring the hot filtrate solution into ether. The crystals were collected and dried in vacuum yielding 0.6 g. Based upon the expected formula of C19H11BrIN7O6, the expected elemental analysis is 35.65% C, 1.73% H, 15.32% N and 15% O. Observed were 35.9%, 2.03%, 12.42% and 16.67%, respectively. The product showed a melting point over the 210-217 degree centigrade range, indicating greater than 98% purity. Thin layer chromatography (n-butanol:acetic acid:water at a 78:5:17 volume ratio) showed a single spot with a retention factor of 0.73. U.V. analysis in methanol:water (1:1 by volume) showed a maximum lambda at 240.5 nm and a molar extinction coefficient of 28,600.

Example 2

Conversion Of INDT To Formazan

One technique used to reduce the chromogen INT to the corresponding formazan is mixture with ascorbic acid. Ascorbic acid is a stronger reductant at pH 5.0 than at pH 3.0: at pH 3.0 ascorbic acid will not appreciably reduce INT to formazan in 60 minutes; at pH 5.0, ascorbic acid will reduce INT to formazan in 30 minutes.

INDT was dissolved in water (0.5 mg/ml) and this solution was brought to pH 3.0 with hydrochloric acid. Ascorbic acid (a saturated solution in water) was then added. Within 30 minutes, a dark red formazan derivative appeared as an insoluble precipitate.

Example 3

To test the histochemical usefulness of INDT formalin fixed, paraffin embedded tissue sections of small bowel, known to contain a high content of intestinal alkaline phosphatase were dewaxed and hydrated to IX Automation Buffer (Biomeda Corp.). The tissues were then dipped into a mixture of 5 bromo -4-chloro-3-indolylphosphate (BCIP) containing either iodonitrotetrazolium (INT) or the new INDT compound prepared as follows.

Making a stable BCIP/INDT solution was accomplished in the following manner. To a 25 mg INDT solution in absolute dimethylformamide (Ultrapure from Amresco) was added 10 to 20 mg of saponin and stirred it until it dissolved. The solution was stable under storage at room and refrigeration temperatures. To 15 ml of a 0.1M Tris HCl pH9.5 buffer containing 0.1M NaCl and 5mM MgC12 was added 50 microliters of a 50 mg BCIP per ml absolute DMF solution. After mixing slowly for 10 seconds, 100 microliters of the INDT/DMF solution containing saponin was added. The INDT went into solution and stayed there.

The results of microscopic examination revealed that intestinal brush borders in both instances turned brown, using either BCIP/INT or BCIP/INDT as the chromogen, indicating the precise and expected localization of intestinal alkaline phosphatase. There was some blue coloration in the INDT treated sample indicating that the reduction was not as efficient as INT and resulted in some blue BCI being deposited at the site of enzyme activity. [If tissue sections were placed for 5 minutes in 1% acid alcohol (1% HCl in 70% ethanol/H20) then tissue could not be stained. This is because exposure of the tissues to acid destroyed the natural alkaline phosphatases in the tissues). The precipitate in both instances was soluble in 95% alcohol whether it was INT or the new INDT. The two color products on the slides did not fade in the following six weeks when they were wet mounted in Crystal/Mount (Biomeda Corp.). No immediate advantage for INDT appears in these tests.

This demonstration did show however that INDT was capable of specific enzyme localization on tissue sections. It showed that the brown product was easily visible by light microscopy. The INDT did not produce any background staining in the short run. Stock solutions of INDT are stable in storage under the right conditions. Showing that INDT does precipitate in the McGadey reaction is proof of its tetrazolium nature. This means that it should work in a similar manner on any reaction such as acid phosphatase, oxidases, and peroxidases.

Example 4

1 microliter spots of goat anti mouse conjugated alkaline phosphatase at 1.0 mg per ml in 1X Automation buffer. (a product of Biomeda Corporation containing 0.1 m Tris HCL, pH 7.5, 0.1 M NaCl and 2.5 ml/l Brij 35 in water) containing 1mM MgCl2 were pipetted onto dry nitrocellulose membranes and allowed to air dry. The papers were then reacted with a solution of BCIP/INT or BCIP/INDT constructed as above in 0.1M Tris HCl buffer pH 9.5 containing 5 mM MgCl2. Both papers rapidly turned brown in the areas where the spots of alkaline phosphatase had immobilized. The INDT treated paper often had a center of blue with a brown ring around it; indicating that in the area of high alkaline phosphatase activity only BCI was deposited without INDT reduction. The INT spot was uniformally brown. This means that INDT will precipitate when low levels of alkaline phosphatase are found on a solid surface and it may be paradoxically inhibited at higher alk. phos. concentrations. The paper did pick up a slight general brown appearance in the INDT solution which was present on the paper in the INT solution. Therefore, INDT had less stability under the conditions chosen. This appears to be directly related not to reduction power but to solubility. Saponin did improve the chromogen stability. Biotin labelled goat anti-rabbit antibodies and biotin labelled whole human genomic DNA were also immobilized onto nitrocellulose membranes and localized with a 1:200 dilution avidin conjugated to alkaline phosphatase (Biomeda Corp.) in primary antibody diluent (Biomeda Corp.) 1 nanogram spots of these biotin labelled materials could be localized with the BCIP/INDT chromogen but there was a 1+background. BCIP/INT solutions were just as sensitive but did not have this background. More work is needed to stabilize the INDT chromogen in solution in order to improve its performance on membrane surfaces. This work indicates that both Western, Southern, and dot blot nitrocellulose membrane formats will succeed using INDT as the detection chromogen.

Example 5

Membranes from Example 4 or tissue sections from Example 3 placed in 95% alcohol lost their INDT chromogen from the paper or tissue surfaces. The INDT entered the solution of 95% alcohol quite rapidly to produce a uniform red color which has been stable for weeks at room temperature. This red-brown color can be read in a spectrophotometer at 443nm. A shift in the absorbance evidences uniqueness of the INDT compound over standard INT. INDT therefore can be made into an ELISA assay detection system by either developing the enzyme in an organic based solvent system or by adding it to the organic solvent after a solid phase water-based chromogen reaction has taken place. The latter format yields maximum emzyme activity and chromogen placement.

Example 6

The procedures of Brigati, D.J., et al, Immmunocytochemistry is Automated: Development of a Robotic Workstation based upon the Capillary action principle, *J. of Histotechnology* 11(3) 165–183 (1988), were followed on Fisher Scientific Company's CODE-ON instrument except that alkaline phosphatase conjugated goat anti-mouse antibodies were used instead of the AutoProbe horseradish peroxidase system. Monoclonal antibodies against muscle specific actin at a 1:10,000 dilution (a gift of Alan Gown, M.D.) were reacted on sections of small bowel and localized with a 1:1000 dilution alkaline phosphatase conjugated goat anti-mouse antibodies (Biomeda Corp., Foster City, Calif.). Each incubation was for 30 minutes at 40 degrees C. in 1X Automation buffer (Biomeda Corp.) A solution of BCIP/INDT made as stated above was then incubated with the tissue sections at two ten minute applications at 45 degrees C. The sections were then counterstained with Hematoxylin (Biomeda Corp.) and embedded in Crystal/Mount (Biomeda Corp.) The BCIP/INDT chromogen had to be made fresh to work best.

A strong brown stain resulted over the smooth muscle in the bowel wall and in blood vessels and myoepithelial cells. This same exact localization had been seen for months using the standard horseradish peroxidase based AutoProbe system on the same tissue. There was slight background on the tissues. Since the initial experiment, we have used monoclonal antibodies against Leukocytle Common Antigen (Biomeda Corp.) and AE1, AE3 keratin (Biomeda Corp.). The same BCIP/INDT system has localized these primary antibodies.

Example 7

The procedures of Unger et al (*J. of Histotechnology* 11(4), 253-257) were used to localize biotin labelled whole human genome in tissue sections using INDT instead of INT in the alkaline phosphatase chromogen. The INDT did produce a blue-brown product at the site of hybridization of the biotin labelled probe. This indicated again partial reduction.

What is claimed is:

1. A compound of the formula DNB-TZ(P2)(P3) X, wherein TZ is a tetrazolium ring, DNB is 5-(2,4-dinitrophenyl), X is halide, P2 is 2-halophenyl and P3 is 3-nitrophenyl, 3-dinitrophenyl or 3-phenyl.

2. The compound of claim 1 wherein X is Br.

3. The compound of claim 2 wherein P2 is 4-halophenyl and P3 is 4-nitrophenyl.

4. The compound of claim 3 wherein P2 is para-iodophenyl.

5. The compound of claim 1 wherein P2 is para-halophenyl and P3 is 4-nitrophenyl.

6. The compound of claim 5 wherein P2 is para-iodophenyl.

7. A method for staining tissue which comprises:
    a) contacting tissue with the tetrazolium compound of claim 1, and
    b) reducing the tetrazolium compound to formazan to stain the tissue.

8. The method of claim 7 wherein the reducing step (b) comprises introducing a reductant in solution.

9. The method of claim 7 wherein the tissue has an enzyme localized thereon and wherein an enzymatic reactant is introduced with the tetrazolium compound; the enzyme converting the enzymatic reactant to reductant in the vicinity of the enzyme.

10. The method of claim 9 wherein the enzyme is alkaline phosphatase and the enzymatic reactant is 5-bromo-4-chloro-3-indolylphosphate.

11. The method of claim 10 wherein X is Br.

12. The method of claim 11 wherein P2 is para-halophenyl and P3 is para-nitrophenyl.

13. The method of claim 12 wherein P2 is para-iodophenyl.

14. The method of claim 9 wherein X is Br.

15. The method of claim 14 wherein P2 is para-halophenyl and P3 is 4-nitrophenyl.

16. The method of claim 15 wherein P2 is para-iodophenyl.

* * * * *